United States Patent [19]

Mergens et al.

[11] Patent Number: 4,681,756

[45] Date of Patent: Jul. 21, 1987

[54] PREVENTION OF N-NITROSO COMPOUND FORMATION IN VIVO

[75] Inventors: William J. Mergens, West Caldwell; Harold L. Newmark, Maplewood; Prabhakar R. Sheth, Pearl River; Jacques L. Tossounian, Pine Brook, all of N.J.

[73] Assignee: Hoffman-La Roche Inc., Nutley, N.J.

[21] Appl. No.: 880,356

[22] Filed: Jun. 26, 1986

Related U.S. Application Data

[63] Continuation of Ser. No. 744,720, Jun. 14, 1985, abandoned, which is a continuation of Ser. No. 462,290, Jan. 31, 1983, abandoned, which is a continuation of Ser. No. 258,962, Apr. 29, 1981, abandoned.

[51] Int. Cl.⁴ ..................... A61K 9/22; A61K 31/555; A61K 31/34
[52] U.S. Cl. .................................. 424/451; 514/458; 514/474; 424/464
[58] Field of Search .................. 514/474, 458; 424/19

[56] References Cited

FOREIGN PATENT DOCUMENTS 1444024 7/1976 United Kingdom .

OTHER PUBLICATIONS

Physicians' Desk Ref. Non Prec. Drugs, p. 601, 1982.
Ramm et al., Tox. and App. Pharm., 41:575-583, 1977.
Ohshima et al., Can. Res., 41:3658, 1981.

*Primary Examiner*—Johnnie R. Brown
*Assistant Examiner*—John W. Rollins
*Attorney, Agent, or Firm*—Jon S. Saxe; George M. Gould; Norman C. Dulak

[57] ABSTRACT

The effect of a controlled release, hydrodynamically balanced dosage formulation containing both an aqueous phase N-nitroso compound blocking agent and a lipid phase N-nitroso compound blocking agent in preventing the formation of nitrosamines and nitrosamides in the stomach is disclosed.

4 Claims, No Drawings

PREVENTION OF N-NITROSO COMPOUND FORMATION IN VIVO

This application is a continuation of application Ser. No. 744,720, filed June 14, 1985, now abandoned, which is a continuation of application Ser. No. 462,290, filed Jan. 31, 1983, now abandoned, which in turn is a continuation of Ser. No. 258,962, filed Apr. 29, 1981, now abandoned.

BACKGROUND OF THE INVENTION

Nitrosamines and nitrosamides having a variety of molecular structures, are often toxic to animals and humans. Most nitrosamines and nitrosamides have also been shown to be carcinogenic and usually mutagenic as well.

Under conditions of pH and temperature similar to those found in mammalian stomachs, nitrites react with secondary and tertiary amines to produce nitrosamines. This is potentially detrimental for humans since many foods, particularly cured meats, have sodium nitrite added and many commonly used foods and drugs contain secondary and tertiary amines. Typical of drugs which have such amines are piperazine, phenmetrazine, aminopyrine, primaquine, pemaquine, physostigmine, synephrine, sulfanilylurea, neohydrin, oxytetracycline and the like.

Foods can contain such naturally occurring amines as dimethylamine, diethylamine, trimethylamine, pyrrolidone, piperidine, proline, hydroxyproline, arginine, 2-dimethylaminoethyl acetate, 2-dimethylaminoethanol, methyl ester of N,N-diethylglycine, N,N-dimethylglycine and the like.

Similar nitrosation reactions can occur with amides, particularly secondary amides, to form N-nitrosamides, most of which have been shown to be carcinogenic or mutagenic or both.

Nitrites can also be formed by in vivo reduction of nitrates. Nitrates and nitrites in combination with secondary and tertiary amines are, thus, considered potential precursors in the formation of nitrosamines and nitrosamides. Nitrates are natural constituents of plants and occur in large amounts in many vegetables. Some water supplies also have high nitrate content.

Nitrite is also formed in the human mouth by the action of oral bacteria in reducing nitrate to nitrite. This production of salivary nitrite can persist for many hours due to the recycling of dietary nitrate into the saliva. Nitrite can also be formed from nitrate in vivo in the stomach itself by the action of bacterial flora, when the pH of the stomach rises for a prolonged period of time. This pH rise in the stomach, or achlorhydria, may be the result of disease (i.e., pernicious anemia, chronic atropic gastritis, etc.) or induced by drugs (e.g. cimetidine). Thus, a substantial amount of nitrite can pass into the stomach over a 24 hour period.

N-nitroso compounds (nitrosamines and nitrosamides) are a unique group which includes very highly potent carcinogenic agents. Once formed and present in vivo, these N-nitroso compounds are not easily or readily converted back to their precursors. Instead, they metabolize in vivo to, or are otherwise converted to, alkylating agents which are the terminal or proximal carcinogens. Control of the N-nitroso carcinogenic compounds has, to date, depended on the use of blocking agents that prevent their formation, i.e. by preferentially, reacting with the nitrosating agent. As discussed above, nitrites in the stomach, from, e.g. food additive use, from microbiological or enzymatic conversion of nitrate in saliva or the stomach itself, are a source of nitrosation for susceptible amines or amides to produce, in the stomach, the N-nitroso carcinogenic compounds.

This invention is directed to a means of preventing the in vivo formation of nitrosamines and nitrosamides in the stomach resulting from the concurrent presence, by administration or ingestion, of nitrites and amines. To be so effective, however, the preventive formulations must be retained in the stomach with the active ingredient, a N-nitroso compound blocking agent, slowly released over an extended period of time in the stomach itself.

In most controlled release preparations known to the pharmaceutical art, the active ingredients are either coated with varying thicknesses of some type of relatively insoluble material or are imbedded into a rigid lattice of resinous material. In such preparations, the object is to continuously provide drug for absorption into the blood stream to replace the amount eliminated while the dosage form is passing through the gastrointestinal tract of the patient.

Such conventional formulations, which are not specifically retained in the stomach and which release medicament in the intestines or during passage in most of the gastrointestinal tract, are not suitable for use in the method of this invention wherein the active ingredient must be retained specifically in the stomach for continuous release over long periods in the stomach itself.

In the controlled release formulations used in the practice of this invention, formulations contained in capsules or tablets remain buoyant and freely floating in the gastric fluid for an extended period of time during which substantially all of the active ingredient contained in the formulations is released in the gastric fluid.

Formulations, either capsules or tablets, which remain intact and buoyant in the gastric fluid while substantially all of the medicament is released therefrom are described in the art. See, for example, U.S. Pat. Nos. 4,126,672; 4,140,755 and 4,167,558 where formulations for the preparation of controlled release capsules or tablets for oral administration are described.

The capsules are hydrodynamically balanced to have a bulk density (specific gravity) of less than one when in contact with gastric fluid and, therefore, will remain floating in gastric fluid which has a specific gravity of between 1.004 and 1.010. These controlled release capsule formulations comprise a homogeneous mixture of one or more medicaments with one or more hydrophilic hydrocolloids. Upon dissolution of the gelatinous capsule and contact of the formulation with the gastric fluid, the capsule will form on its surface a soft gelatinous mass, maintaining the shape of the capsule. The medicament is slowly released from the surface of the gelatinous mass which, due to its density, remains buoyant in the gastric fluid. Ultimately, after substantially all of the medicaments therein are released, the gelatinous mass disperses.

Hydrodynamically balanced tablets can be made on conventional tableting equipment. It is critical that the tablets are compressed to a degree of hardness such that they will acquire a bulk density of less than one in contact with gastric fluids. However, tablets which initially have a density greater than one will be buoyant in gastric fluids. This buoyancy results from a combination of an increase in the bulk volume of the tablet when it contacts gastric fluids due to the hydration and swelling of the hydrocolloid particles on the tablet surface and the internal voids in the tablet center remaining dry due to the barrier formed by the hydrocolloid particles. Therefore, it is critical that the tablets are not compressed to a degree of hardness such that the porosity is materially reduced and the hydrocolloid particles on the tablet surface are compacted so tightly that rapid hydration is retarded. It will be appreciated that the maximum hardness to which a tablet having an initial density greater than one can be compressed will vary both with the initial density of the formulation and the size of the tablet. The hardness for any tablet will be between the maximum at which a buoyant tablet can be produced in accordance with the teachings herein and a minimum required for tablets to meet basic pharmaceutical tests of stability during shipping and the like. This range of hardness can be easily determined by standard pharmaceutical hardness measurements combined with testing of the buoyancy of samples of tablets of different hardness in gastric fluid. Such determinations are considered to be within the purview of the skilled artisan.

The hydrated barrier layer of the outermost hydrophilic colloid slowly dissolves releasing medicament. There is also a release of medicament by leaching action at or near the surface of the mass. As new surface is exposed to gastric fluid it becomes hydrated, thus maintaining the integrity of the barrier. This process is continuously repeated until the medicament is substantially leached out. Thereafter the remaining matrix which is still buoyant in gastric fluid slowly disperses and is eliminated. It has been found that the release pattern and resulting blood levels attained with these hydrodynamically balanced controlled release formulations have advantages over other controlled release mechanisms.

To prevent the formation of N-nitroso carcinogenic compounds in the stomach, block agents are used. These blocking agents act primarily either in the aqueous phase or in the lipid phase of the gastric fluid. Aqueous phase N-nitroso compound blocking agents include sulfite, bisulfite, cysteine, certain phenols such as gallic acid, tannic acid and the like, ascorbic acid (vitamin C) and its salts, erythorbic acid and its salts, ferulic acid and its salts, caffeic acid and its salts and the like. Lipid phase N-nitroso compound blocking agents include the free tocopherols, particularly alphatocopherol (vitamin E), propyl gallate, ascorbyl palmitate, ascorbic acetals of C-8 to C-16 aldehydes, ethoxyquin, tertiary butyl hydroxyquinone, nor-dihydroguariaretic acid (NDGA), 8-hydroxyquinoline and the like.

The use of such materials as blocking agents in preventing N-nitroso compound formation is well known in the art. Detailed summaries of such use are found in: Newmark, H. L. and Mergens, W. J., *Applications of Ascorbic Acid and Tocopherol as Inhibitors of Nitrosamine Formation and Oxidation in Foods;* In *Criteria of Food Acceptance,* ed. by J. Solms and R. L. Hall, Switzerland, Forster Verlag AG/Forster Publishing Co., 1951; *Alpha-Tocopheral (Vitamin E) and Its Relationship to Tumor Induction and Development* ed. by M. Zedech and M. Lipkin, New York, Plenum Press, 1981 (in press) and Douglas, M. L. et al. *The Chemistry of Nitrosamine Formation, Inhibition and Destruction,* in J. Soc. Cosmet. Chem. 28:p 581, 1978.

Among the medicaments listed in U.S. Pat. Nos. 4,126,672, 4,140,755 and 4,167,558 as possible active ingredients amenable to use in controlled release formulations are the vitamins used as nutritional supplements. There is, however, no disclosure of formulations containing combinations, as aqueous phase and lipid phase N-nitroso compound blocking agents, of the specific vitamins C and E used as safe chemical agents for the prevention of the formation of N-nitroso compounds in the stomach nor is there any disclosure of the quantity or ratio of these vitamins in the formulations.

DETAILED DESCRIPTION OF THE INVENTION

This invention is based on the discovery that in vivo nitrosamine or nitrosamide formation resulting from the substantially concurrent administration or ingestion of nitrites and/or nitrates and secondary amines, secondary amides or tertiary amines is significantly inhibited by the oral administration of a controlled release, hydrodynamically balanced capsule or tablet containing, as the active ingredients, a combination of an aqueous phase N-nitroso compound blocking agent and a lipid phase N-nitroso compound blocking agent.

This combination of the aqueous phase and lipid phase blocking agents, resulting in an additive action against formation of nitrosamine and nitrosamide compounds, is needed since the food mixtures normally present in the stomach contain both aqueous and lipid phases.

Of the known blocking agents, ascorbic acid or its salts, and α-tocopherol (vitamin E) are the preferred blocking agents for long term administration. These compounds are known to be safe for long term intakes at high levels. They are also present in food, albeit at lower levels, and are, thus, a major part of the "natural" blocking agent capacity of fresh foods and, in particular, uncooked foods.

The use of vitamin C and vitamin E in combination is especially preferred. Ascorbic acid (vitamin C) functions primarily in the aqueous phase while α-tocopherol (vitamin E) functions primarily in the lipid phase.

These hydrodynamically balanced controlled release formulations comprise a mixture of the active ingredients with one or more hydrophilic hydrocolloids.

Hydrocolloids suitable for use in these controlled release formulations include one or more natural, partially or totally synthetic anionic or, preferably, nonionic hydrophilic gums, modified cellulosic substances or proteinaceous substances such as, for example, acacia, gum tragacanth, locust bean gum, guar gum, karaya gum, agar, pectin, carrageen, soluble and insoluble alginates, methylcellulose, hydroxypropyl methylcellulose hydroxypropylcellulose, sodium carboxymethylcellulose, carboxypolymethylene (Carbopol-Cabot Corporation), gelatin, casein, zein, bentonite, Veegum (R. T. Vanderbilt Co.) and the like. A preferred hydrocolloid is hydroxypropyl methylcellulose. The use of such materials in pharmaceutical compounding is also known in the art. For example, Kaplan et al. U.S. Pat. No. 3,555,151 discloses the use of such hydrocolloids in controlled release antacid preparations.

The hydrocolloids utilized must hydrate in acidic medium, i.e., gastric fluid with a pH equivalent to 0.1N hydrochloric acid (pH of approximately 1.2). Furthermore, although the bulk density of the controlled release formulation may initially be greater than one, it is essential that the dosage forms be hydrodynamically balanced to have a bulk density of less than one when in contact with gastric fluids to assure buoyancy. There are a number of methods whereby the rate of release of medication from the sustained release formulation can be adjusted. First, the choice of a particular hydrocolloid or mixture of hydrocolloids can affect the release rate, e.g., high viscosity hydrocolloids, such as hydroxypropylmethylcellulose, 4000 cps, hydrate more slowly and maintain a soft mass for a longer time than low viscosity hydrocolloids, such as hydroxypropyl methylcellulose, 10 cps. Further, edible, pharmaceutically inert, fatty materials having a specific gravity of less than one can be added to the formulation to decrease the hydrophilic property of the formulation and therefore increase buoyancy. Examples of such materials include a purified grade of beewax; fatty acids; long chain fatty alcohols; glycerides such as glyceryl esters of fatty acids as, for example, glyceryl monostearate, glyceryl distearate, glyceryl esters of hydrogenated cottonseed oil and the like and oils such as mineral oil and the like.

There may also be incorporated in these controlled release formulations additional edible nontoxic ingredients recognized in the art of pharmaceutical compounding such as excipients, i.e., buffering agents, preservatives, stabilizers, tabletting lubricants and the like.

The amount of hydrocolloid ingredient present in these controlled release formulations may vary within a wide range, i.e., from about 5% by weight to about 90% by weight. The amount of hydrocolloid will vary in relation to the amounts and properties of the active ingredient and inert pharmaceutical adjuncts utilized. Generally, the amount of hydrocolloid will be between about 15% by weight and about 75% by weight.

When a fatty material or a mixture of fatty materials is present in the controlled release formulations, such material comprises up to about 60% by weight of the total formulation. In general, when the formulations contain a fatty material, such material is present in from about 5% by weight to about 30% by weight. The amount of fatty material is governed by the amounts and physical characteristics of both the active ingredient and the hydrocolloid with the object being to achieve a hydrodynamically balanced formulation, i.e., a formulation which acquires a bulk density of less than one in gastric fluids.

The amount of edible inert pharmaceutical adjunct materials which may be present in the controlled release formulations will also vary in accordance with the amounts and physical properties of the other ingredients. Such materials which themselves have a bulk density of less than one, e.g., ethylcellulose or other low bulk density materials, will enhance the buoyancy of the formulation. It is possible to utilize the selection of inert pharmaceutical adjunct materials to modify the rate of release of the formulation. For example, soluble excipients, e.g., lactose, mannitol and the like, will increase the rate of release. When such pharmaceutical adjunct materials are included in the formulations, they can be present in up to 80% by weight of the final formulation. Generally, such conventional pharmaceutical adjuncts are present in from about 5% by weight to about 60% by weight of the formulation. The inclusion of and choice of such materials is again considered to be within the purview of the art.

The controlled release dosage forms are particularly amenable to the administration of medicaments which are only absorbed through the stomach or upper portion of the intestines, e.g. ferrous salts such as ferrous fumarate, or which exert a therapeutic effect in the stomach, for example, antacids such as the oxides, hydroxides and carbonates of magnesium, aluminum hydroxide, magnesium trisilicate and the like. When such substances generate carbon dioxide, bubbles will become entrapped by the hydrated outer layer and, thus, enhance the buoyancy of the tablet. Small amounts of carbon dioxide generating bases can also be utilized in non-antacid formulations to enhance buoyancy as long as the resulting density of the dosage form is not too high.

The quantity of active ingredient present is usually between 10% by weight and 80% by weight based on the total weight of the formulation. The quantity of the preferred active ingredient, i.e., the combination of vitamin C and vitamin E, can range from about 20% by weight to about 60% by weight. The amounts of active ingredients present in the controlled release formulations are determined by such factors as the quantity needed to provide full protection against N-nitroso compound formation over a specified period, and, in reference to the controlled release formulation itself, the bulk density, the hydrophilic or hydrophobic properties, the stability and the like. One skilled in the art either knows or can readily ascertain these properties.

When used in combination, the weight ratio of aqueous phase blocking agent to lipid phase blocking agent can also vary. Although a ratio of 1:1 is preferred, the ratio can range from about 10:1 to about 1:10. These same ratios hold for the combination of vitamin C and vitamin E.

The actual amounts of the combination of aqueous phase blocking agent and lipid phase blocking agent orally administered to a subject on a daily basis, from a hydrodynamically balanced, controlled released capsule or tablet, can also vary within wide limits depending chiefly on the amounts needed to afford full protection against N-nitroso formation. This, in turn, depends on the nitrite concentration present in the stomach which varies greatly due to variations in nitrite and nitrate in foods, nitrate conversion by oral microflora to nitrite in saliva, microbial conversion of nitrate to nitrite in stomach contents and the like. The "blocking reaction" against N-nitroso compound formation depends on several factors, particularly on nitrite concentration and, especially, peak nitrite concentration. For full protection, the blocking agents should be almost always present in concentrations sufficient to block all potential nitrosations, including that at the highest potential nitrite concentration. The amount of the combination administered on a daily basis can range from about 25 mg to about 3500 mg of each with the preferred daily amount administered being about 600 mg of each. In the case of the preferred combination of vitamin C and vitamin E, the amount administered on a daily basis ranges from about 25 mg to about 2500 mg of each with the preferred daily amount being about 400 mg of each.

The hydrodynamically balanced controlled release formulations are prepared by techniques well established in the art. In most instances, all that is required is the thorough mixing of all ingredients to form a homogeneous mixture and milling or comminuting the mixture to a relatively fine particle size, i.e. all particles passing a 100 mesh screen. Milling the mixture to a very fine particle size, particularly with the hydrocolloids, does not detract from the controlled release mechanism and in fact exerts a positive effect thereon. The powder mix is then poured into hard shell capsules.

Under certain circumstances the conventional pharmaceutical techniques of slugging, wet granulating or extruding may be required to achieve proper fill or to prepare tablets. However, in any of these procedures, it is essential that the hydrocolloid not be entrapped within the granules to avoid subsequent difficulty of hydration when the dosage form is in contact with gastric fluid. For tablets, the ingredients are, preferably, granulated and the composition is then compressed into tablets of acceptable hardness.

Since the hydrodynamically balanced capsule or tablet is designed to remain in the stomach over prolonged periods of time, the efficacy in such capsules or tablets of the combination of vitamin C and vitamin E in combatting in vivo N-nitroso formation is enhanced. For example, using a simulated stomach apparatus, the inhibition of nitrosamine or nitrosamide formation was significantly prolonged using the hydrodynamically balanced formulation as compared to the efficacy of a chewable tablet containing the same amounts of vitamin C and vitamin E.

The following Examples illustrate the invention.

EXAMPLE 1

The following formulations were prepared to be used in the nitrosamine inhibition studies.

| Chewable Vitamin C and Vitamin E Tablet | |
|---|---|
| Ingredient | Mg./tablet |
| d,l-α-tocopherol, 33⅓% dry powder | 327.1 |
| Microcrystalline cellulose | 100.0 |
| Ascorbic acid, 90% | 40.8 |
| Sodium ascorbate | 77.0 |
| Strawberry flavor | 8.0 |
| Silicon dioxide | 15.0 |
| Fructose | 295.0 |
| Sorbitol | 295.0 |
| FD&C Red #3 | 1.2 |
| Magnesium stearate | 3.0 |
| Total | 1162.1 |

The microcrystalline cellulose, sodium ascorbate, silicon dioxide and FD&C Red #3 were mixed by milling. The d,l-α-tocopherol and ascorbic acid were added to this mixture and mixed therein. Fructose and sorbitol were then milled and thoroughly admixed with the above materials. Finally, the strawberry flavor and magnesium stearate were added separately and mixed.

The formulation was compressed into tablets.

| Hydrodynamically Balanced Tablet Containing Vitamin C and Vitamin E | |
|---|---|
| Ingredient | Mg./tablet |
| Ascorbic acid | 100 |
| D,l-α-tocopherol, 40% dry powder | 250 |
| Magnesium-aluminum silicate complex | 30 |
| Carboxymethylcellulose | 50 |
| Alcohol | q.s. to granulate |
| Ethylcellulose | 15 |
| Carboxypolymethylene | 15 |
| Hydroxypropyl methylcellulose | 145 |
| Magnesium carbonate | 38 |
| Magnesium stearate | 3 |
| Silicon dioxide | 2 |
| | 648 |

The ascorbic acid, tocopherol, aluminum silicate, carboxymethylcellulose, ethylcellulose and carboxypolymethylene were milled, mixed and granulated with alcohol. The admixture was dried overnight at 45° C. The remaining ingredients were mixed therein and the resulting formulation was compressed into tablets having a hardness of 7-14 SCU.

EXAMPLE 2

This Example illustrates the efficacy of the combination of vitamin C and vitamin E in hydrodynamically balanced tablet dosage forms in inhibiting the formation of nitrosamines and compares such hydrodynamically balanced tablet dosage forms with standard chewable tablets containing the same active ingredients.

For this evaluation, a simulated stomach apparatus was prepared. 200 ml of USP simulated gastric fluid in a 500 ml vessel are maintained at 37±1° C. using a constant temperature bath. Simulated gastric fluid is prepared by dissolving 2.0 grams of sodium chloride and 3.2 grams of pepsin in 7.0 ml of hydrochloric acid and sufficient water to make 1000 ml. This fluid has a pH of about 1.2.

During the course of the evaluation equimolar quantities of sodium nitrite and aminopyrine are pumped into the 500 ml vessel containing the gastric fluid. The aminopyrine-nitrile interaction is a very sensitive nitrosation. Aminopyrine is a tertiary amine having a dimethylamino moiety which reacts rapidly with a nitrosating agent over a wide pH range to form dimethylnitrosamine (NDMA).

An output flow is adjusted to equal the sum of the nitrite and amine input and thus maintain a constant 200 ml volume in the reaction vessel over the course of the evaluation. This also simulates the normal transit flow of liquid through the stomach.

The output is collected at predetermined time intervals in stirred vessels containing ammonium sulfamate. Ammonium sulfamate acts as a quenching reagent to stop nitrite-amine interaction after the solution leaves the stomach apparatus and prior to analysis.

To maintain a constant volume, the input and output were matched by using an autoanalyzer pump and calibrated delivery tubings.

The input tubes delivered 0.105 ml of sodium nitrite and 3.4 ml of aminopyrine per minute, respectively. They are taped to the opposite walls of the reaction vessel, with their tips immersed just below the liquid level. The output tubing (flow rate 3.505 ml/minute) is taped to the wall with the tip at the bottom of the vessel. Taping prevents the three tubes from entanglement in the stirring apparatus.

The tablets to be evaluated were placed in a basket which was totally immersed in the 200 ml of gastric fluid. The basket was attached to the end of a stirring rod and rotated at 100 rpm to facilitate dissolution and dispersion. (USP-Rotating Basket apparatus). In the control, i.e., no N-nitroso compound blocking agent present, the empty rotating basket apparatus was employed to keep conditions consistent.

The actual amounts of sodium nitrite and aminopyrine added are summarized in Table I below. The rate of addition of sodium nitrite was 2.04 mg/hour or the equivalent of 49 mg/day. The output volumes collected were extracted with methylene chloride. Dimethylnitrosamine (NDMA) measurements were made using a gas chromatography-thermal energy analyzer (GC-TEA) on a 10'×⅛" 10% carbowax 20M column operated isothermally at 165° C.

TABLE I

| Solution | Concentration, mg/ml | Addition Rate, ml/min | Total mg/hr | Concentration, mM/Hr |
| --- | --- | --- | --- | --- |
| I. Sodium nitrite in water | 0.325 | 0.105 | 2.04 | 0.0296 |
| II. Aminopyrine in USP gastric fluid | 0.0335 | 3.4 | 6.83 | 0.0296 |

The N-nitroso inhibitory action of chewable tablets containing 100 mg of vitamin C and 100 mg of vitamin E were compared to hydrodynamically balanced tablets containing 100 mg of vitamin C and 100 mg of vitamin E. The results are reported in Table 2 as the percent dimethyl nitrosamine (NDMA) inhibition compared to nitrosamine formation in the absence of a blocking agent.

TABLE 2

| Formulation | Elapsed time hrs | % NDMA Inhibition |
| --- | --- | --- |
| Chewable tablet | 1 | 100 |
|  | 2 | 100 |
|  | 3 | 73 |
|  | 4 | 44 |
| Hydrodynamically balanced tablet | 1 | 100 |
|  | 2 | 100 |
|  | 3 | 99 |
|  | 4 | 97 |

We claim:

1. A method for preventing or inhibiting the formation in vivo in the stomach of nitrosamines and nitrosamides resulting from the presence in mammals of nitrites and secondary amines, tertiary amines or secondary amides which comprises orally administering to said mammals, on a daily basis, an amount of a combination of vitamin C and vitamin E which is effective in preventing or inhibiting the formation in vivo of nitrosamines and nitrosamides, said combination being administered in the form of a controlled release, hydrodynamically balanced tablet or capsule in which the ratio of vitamin C to vitamin E ranges from about 10:1 to about 1:10.

2. The method of claim 1 wherein the aqueous phase N-nitroso blocking agent is vitamin C, the lipid phase N-nitroso blocking agent is vitamin E, and the amount of each of such vitamins administered on a daily basis ranges from about 25 mg to about 2500 mg.

3. The method of claim 2 wherein the amount of the combination of vitamin C and vitamin E administered on a daily basis is 400 mg of each.

4. The method of claim 1 wherein the ratio of vitamin C to vitamin E in the combination is 1:1.

* * * * *